(12) United States Patent
Miyamoto et al.

(10) Patent No.: US 9,833,401 B2
(45) Date of Patent: Dec. 5, 2017

(54) METHOD FOR PRODUCING COMPOSITION FOR EXTERNAL USE CONTAINING PHYSIOLOGICALLY ACCEPTABLE SALT OF TRANEXAMATE

(75) Inventors: Masayoshi Miyamoto, Hyogo (JP); Tomomi Kuromiya, Mie (JP); Daisuke Suzuki, Yamanashi (JP)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 37 days.

(21) Appl. No.: 13/814,549

(22) PCT Filed: Jul. 15, 2011

(86) PCT No.: PCT/IB2011/001865
§ 371 (c)(1),
(2), (4) Date: Feb. 6, 2013

(87) PCT Pub. No.: WO2012/017313
PCT Pub. Date: Feb. 9, 2012

(65) Prior Publication Data
US 2013/0142741 A1    Jun. 6, 2013

(30) Foreign Application Priority Data

Aug. 6, 2010  (JP) ................. 2010-177580

(51) Int. Cl.
| | | |
|---|---|---|
| *A61K 8/81* | (2006.01) | |
| *A61K 8/41* | (2006.01) | |
| *A61K 8/73* | (2006.01) | |
| *A61Q 19/02* | (2006.01) | |
| *A61K 8/00* | (2006.01) | |
| *A61K 8/84* | (2006.01) | |
| *A61K 8/02* | (2006.01) | |

(52) U.S. Cl.
CPC .......... *A61K 8/8152* (2013.01); *A61K 8/0295* (2013.01); *A61K 8/41* (2013.01); *A61K 8/73* (2013.01); *A61K 8/84* (2013.01); *A61Q 19/02* (2013.01); *A61K 2800/49* (2013.01); *A61K 2800/805* (2013.01)

(58) Field of Classification Search
None
See application file for complete search history.

(56) References Cited

U.S. PATENT DOCUMENTS 5,288,423 A    2/1994  Behan et al.

FOREIGN PATENT DOCUMENTS

| | | |
|---|---|---|
| EP | 0 466 235 A1 | 1/1992 |
| JP | 04-46144 A | 2/1992 |
| JP | 05-194989 A | 8/1993 |
| JP | 2002-234836 A | 8/2002 |
| JP | 2003-306419 A | 10/2003 |
| JP | 2004-107262 A | 4/2004 |
| JP | 2004-277375 A | 10/2004 |
| JP | 2006-045079 A | 2/2006 |
| JP | 2006-306744 A | 11/2006 |
| WO | 00/57841 A1 | 10/2000 |
| WO | WO 2006067945 A1 * | 6/2006 |
| WO | 2006/114338 A1 | 11/2006 |
| WO | 2011/069915 A1 | 6/2011 |

OTHER PUBLICATIONS

International Search Report, dated Feb. 15, 2013, from corresponding PCT application.
"Bright White EX", Mintel, Mar. 2009, http://www.gnpd.com, XP-002691219.

* cited by examiner

*Primary Examiner* — David J Blanchard
*Assistant Examiner* — Sarah Chickos
(74) *Attorney, Agent, or Firm* — Young & Thompson

(57) ABSTRACT

A composition for external use containing a tranexamate as an active ingredient with suppressed sticky or oily feeling but having a fresh feel of use, and a method for producing the same. A tranexamate salt can be dispersed stably in an aqueous medium by (a) dissolving the tranexamate salt and an amphiphilic polymer in water, a water-soluble organic solvent or a mixture thereof; and (b) adding a mixed solution obtained in the step (a) to an aqueous medium, and thus keeping the tranexamate salt in molecular assembly particles formed of the amphiphilic polymer.

9 Claims, No Drawings

METHOD FOR PRODUCING COMPOSITION FOR EXTERNAL USE CONTAINING PHYSIOLOGICALLY ACCEPTABLE SALT OF TRANEXAMATE

TECHNICAL FIELD

The present invention relates to a method for producing a composition for external use comprising a physiologically acceptable salt of a tranexamate as an active ingredient, and to the composition for external use and a molecular assembly particle obtained thereby. The present invention also relates to a cosmetic method for inhibiting pigmentation of and/or whitening the skin comprising the topical application to the skin, of said composition for external use.

BACKGROUND ART

Skin-whitening activity of a tranexamate compound is known, and a tranexamate compound has been used as a skin-whitening ingredient in compositions for external use, such as drugs, quasi-drugs, and cosmetics. For example, Japanese Patent Laid-Open No. 04-46144 discloses an anti-pigmentation agent for external use using a tranexamate compound as an active ingredient. Japanese Patent Laid-Open No. 2003-306419 exemplifies tranexamic acid and derivatives thereof as a skin-whitening ingredient to be usable with Coenzyme Q10. Japanese Patent Laid-Open No. 2004-107262 exemplifies cetyl tranexamate as an oil-soluble skin-whitening ingredient to be usable with an L-ascorbic acid tetra-branched fatty acid ester derivative.

However, a tranexamate compound or a salt thereof is sparingly soluble in water or oil, and so it is likely to cause aggregates in a formulation. Thus, it is difficult to incorporate it in a formulation in a homogeneous state.

Japanese Patent Laid-Open No. 2002-234836 discloses an anti-stress external preparation for skin using a tranexamate as an active ingredient. It also discloses a method to dissolve a tranexamate using a large amount of an oil component such as an olive oil. However, by this method, the formulation form is limited to a cream or a milky lotion due to the use of a large amount of an oil component. Additionally, the obtained external preparation is sticky and oily, and very uncomfortable to use.

Further, Japanese Patent Laid-Open No. 2006-306744 discloses an external preparation for skin using a tranexamate or a salt thereof as well as a silicone oil. The same teaches that by the combination of a tranexamate or a salt thereof and a silicone oil, the solubility of the tranexamate or a salt thereof in the composition can be enhanced, and the activity of the tranexamate can last over an extended time period. Although the silicone oil is known as an oil component which is comfortable to use, due to the necessity to use a large amount of silicone oil to dissolve the tranexamate, the range of choice for the skin external preparations becomes narrow.

In the meantime, Japanese Patent Laid-Open No. 2006-45079 describes that a stable cosmetic material can be obtained by using a whitening ingredient such as sodium tranexamate together with a polymer compound having a quaternary amino group such as polyquaternium. However, all the whitening ingredients described here including sodium tranexamate are water-soluble compounds, and thus the problem of dissolution in a formulation does not occur.

The patent application WO00/57841 describes that a polysaccharide-cholesterol derivative can be utilized as a moisture retention ingredient in a cosmetic material. However, it is not described that an ingredient having a low solubility in water and oil can be dispersed in a formulation by using a polysaccharide-cholesterol derivative.

SUMMARY OF THE INVENTION

Under such circumstances, there is a need for a formulation comprising a tranexamate or a salt thereof, which does not provide a sticky or oily feeling, and which gives a fresh and comfortable application. Furthermore, there is a need for a broad range of formulations comprising a tranexamate or a salt thereof, which may be easily formulated.

Surprisingly, the applicant has found that a tranexamate salt can be dispersed stably in an aqueous medium without causing aggregates or crystal precipitation of the tranexamate salt. Said tranexamate salt is dissolved with an amphiphilic polymer in water, a water-soluble organic solvent or a solvent mixture thereof, in a specific condition, and the resulting mixture is added to an aqueous medium.

Thus, the present invention provides a method for producing a composition for external use comprising a physiologically acceptable tranexamate salt mentioned below (also referred to as a "tranexamate salt") as an active ingredient. The present invention also provides a composition for external use obtained by the method, as well as a cosmetic method for inhibiting hyperpigmentation of and/or whitening the skin, or for reducing aging spots or pigmentation spots, by the topical application to the skin of said composition.

The present invention relates to a method for producing a composition for external use comprising a physiologically acceptable salt of a tranexamate, which comprises the steps of:
(a) dissolving a physiologically acceptable salt of a tranexamate (also called "tranexamate salt") and an amphiphilic polymer, at a weight ratio of 1:3 to 1:20, in water, a water-soluble organic solvent or a mixture thereof, so as to obtain a mixed solution; and
(b) adding the mixed solution obtained in step (a) to an aqueous medium.

Preferably, the tranexamate is represented by the following formula (1):

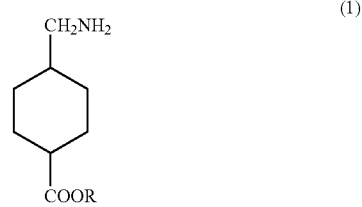

wherein R represents a $C_1$ to $C_{22}$ linear or branched, saturated or unsaturated hydrocarbon group, which may be substituted by a substituent selected from a hydroxyl group and an amino group.

Preferably, the physiologically acceptable salt of the tranexamate is cetyl tranexamate hydrochloride.

Preferably, the amphiphilic polymer is selected from the group consisting of a (2-methacryloyloxyethyl phosphorylcholine/stearyl methacrylate) copolymer and cholesteryl hexyl dicarbamate pullulan.

Preferably, the aqueous medium comprises water in an amount of 60 wt % or more.

Preferably, in step (a), the mixture containing the physiologically acceptable salt of the tranexamate, the amphiphilic polymer and the solvent, is heated at a temperature of from 20 to 120° C. to obtain said mixed solution.

Preferably, step (b) is performed at a temperature of from 50 to 95° C.

Preferably, after step (b), molecular assembly particles comprising the physiologically acceptable salt of the tranexamate are formed.

Preferably, the method according to the invention further comprises a step (c) of adding a composition obtained in step (b) to another composition for external use.

The present invention also relates to a composition for external use obtained by said method.

Said composition for external use preferably comprises the physiologically acceptable salt of the tranexamate in an amount of 0.001 to 5.0 wt %, and the amphiphilic polymer in an amount of 0.01 to 25.0 wt %.

The present invention also relates to the cosmetic use of said composition, for inhibiting pigmentation of and/or whitening the skin, in order to reduce aging spots or pigmentation spots. The present invention also relates to said composition for use for inhibiting pigmentation of and/or whitening the skin, in order to reduce aging spots or pigmentation spots.

The present invention also relates to a cosmetic method for inhibiting pigmentation of and/or whitening the skin, the method comprising the topical application, to the skin, of the composition for external use.

Finally, the present invention also relates to a molecular assembly particle obtained by a method comprising the steps of:

(a) dissolving a physiologically acceptable salt of a tranexamate and an amphiphilic polymer in water, a water-soluble organic solvent or a mixture thereof, at a weight ratio of 1:3 to 1:20, so as to obtain a mixed solution; and (b) adding the mixed solution obtained in step (a) to an aqueous medium.

According to the present invention, the active ingredient derived from a tranexamate (i.e. tranexamate salt) can be dispersed stably in a composition. According to the present invention, the compositions for external use comprising a tranexamate salt can have various galenic forms.

MODES FOR CARRYING OUT THE INVENTION

The invention will be described in more detail below.

The method for producing a composition for external use of the present invention comprises:

a) dissolving a physiologically acceptable tranexamate salt and an amphiphilic polymer, in a weight ratio of 1:3 to 1:20, in water, a water-soluble organic solvent or a mixture thereof, so as to obtain a mixed solution;

b) adding the mixed solution obtained in step a) in an aqueous medium.

Each step will be described below.

Step a)

In step a), a tranexamate salt and an amphiphilic polymer are used in a specific weight ratio and dissolved in water, a water-soluble organic solvent or a mixture thereof.

In the method of the present invention, the tranexamate is preferably represented by the following formula (1):

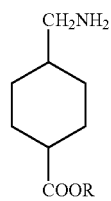

wherein R represents a $C_2$ to $C_{22}$ linear or branched, saturated or unsaturated hydrocarbon group, which may be substituted by a substituent selected from a hydroxy group and an amino group.

In the Formula (1), R represents a C1 to C22 linear or branched, saturated or unsaturated hydrocarbon group, in which a hydrogen atom may be replaced by a substituent selected from a hydroxy group and an amino group.

The hydrocarbon group may be acyclic or cyclic. In case the hydrocarbon group is acyclic, it may be a linear or branched chain. Examples of the hydrocarbon group includes: an alkyl group, an alkenyl group, an alkynyl group, an alkyldienyl group, an aryl group, an alkylaryl group, an arylalkyl group, a cycloalkyl group, a cycloalkenyl group, and a cycloalkylalkyl group. Among them an alkyl group is preferable. The carbon number is preferably 8 to 20, and especially preferably 12 to 18.

There is no particular restriction of the number of substituents on the hydrocarbon group. In case the hydrocarbon group has 2 or more substituents, the substituents may be either hydroxy groups or amino groups, or both of hydroxy group(s) and amino group(s).

Specific examples of the tranexamate represented by Formula (1) include lauryl tranexamate, myristyl tranexamate, cetyl tranexamate and stearyl tranexamate. Among them, cetyl tranexamate is especially preferable.

Although there is no particular restriction on a physiologically acceptable salt of the tranexamate to be used in the present invention, insofar as the object of the present invention is not impeded, preferable examples thereof include a mineral acid salt, such as a hydrochloride salt, a phosphoric acid salt, a sulfuric acid salt, a bromic acid salt, and a nitric acid salt; an organic acid salt, such as an oxalic acid salt, a lactic acid salt, and a citric acid salt; and a carbonic acid salt of a tranexamate.

Among others, a tranexamate salt to be used in the present invention should preferably be selected from the group consisting of cetyl tranexamate hydrochloride salt, cetyl tranexamate phosphoric acid salt, cetyl tranexamate sulfuric acid salt, cetyl tranexamate bromic acid salt, cetyl tranexamate nitric acid salt, cetyl tranexamate oxalic acid salt, cetyl tranexamate lactic acid salt, cetyl tranexamate citric acid salt, and cetyl tranexamate carbonic acid salt. Cetyl tranexamate hydrochloride salt is especially preferable.

The tranexamate salt may be used singly or in combination of two or more types.

In the present invention, the amphiphilic polymer is a polymer having a weight average molecular weight of not less than 10,000, and having both a hydrophilic moiety and a hydrophobic moiety. Preferable examples of the amphiphilic polymer used in the present invention include polymers which self-associate in water, a water-soluble organic solvent or a mixture thereof, to form molecular assembly particles.

The weight average molecular weight of the amphiphilic polymer is preferably 10,000 to 5,000,000, more preferably 30,000 to 2,000,000, and particularly preferably 100,000 to 1,000,000. Here, in the present invention, the weight average molecular weight is determined by gel filtration chromatography (GFC in terms of pullulan conversion).

Examples of the amphiphilic polymer used in the present invention include polyquaternium, which is an amphiphilic polymer compound having a quaternary amino group. Particularly preferably included is polyquaternium-61 ((2-methacryloyloxyethylphosphorylcholine/stearyl methacrylate) copolymer) having a weight average molecular weight of 100,000 to 2,000,000 (preferably 100,000 to 1,000,000) (for example, see Japanese Patent Laid-Open No. 2004-196868).

In addition, as the amphiphilic polymer, a polysaccharide-sterol derivative, for example, cholesterol pullulan can be used (for example, see Kiyoshi Inomata, Fragrance Journal, 30 (7), 74-78 (2002), patent application WO2000/12564). In particular, hexyl dicarbamate cholesteryl pullulan having a weight average molecular weight of 50,000 to 500,000 can be preferably used.

Commercial products can be used as the amphiphilic polymer. Examples thereof include "Lipidure (registered trademark)-S" produced by NOF Corporation (for example, see Hiroki Fukui, Fragrance Journal, 33 (1), 970102 (2005)) and "Meduseeds (registered trademark)-C1" which is an aqueous dispersion of cholesterol pullulan.

The amphiphilic polymer may be used singly or a combination of two or more types.

In the producing method of the present invention, the tranexamate salt and the amphiphilic polymer are used in a weight ratio of 1:3 to 1:20. If the weight ratio is lower, the tranexamate salt cannot be dispersed sufficiently stably, resulting in aggregates or crystal precipitation of the tranexamate salt; and if the weight ratio is higher, the efficiency deteriorates and it may be difficult to dissolve the tranexamate salt in water, a water-soluble organic solvent or a mixture thereof. The tranexamate salt and the amphiphilic polymer are preferably used in a weight ratio of 1:3 to 1:15, more preferably used in a weight ratio of 1:4 to 1:10.

In step a), the tranexamate salt and the amphiphilic polymer are dissolved in water, a water-soluble organic solvent or a mixture thereof.

The water-soluble organic solvent used in the present invention is not particularly limited in so far as it can dissolve a tranexamate salt and an amphiphilic polymer according to the method of the present invention. Examples thereof include lower alcohols, preferably, alcohols having 1 to 5 carbon atoms, such as methanol, ethanol, propanol, isopropanol; polyhydric alcohols such as ethylene glycol, 1,3-butylene glycol, propylene glycol, dipropylene glycol, isoprene glycol, polyethylene glycol, polyoxyethylene methylglucoside, glycerine and diglycerol.

These water-soluble organic solvents may be used singly or a combination of two or more types.

Above all, water, a polyhydric alcohol or a mixture thereof is preferable as the solvent used in step a). The solvent may be chosen appropriately depending on the type of the amphiphilic polymer. For example, it is preferable to use one kind or two or more kinds of polyhydric alcohols as a solvent when (2-methacryloyloxyethyl phosphorylcholine/stearyl methacrylate) copolymer is used as the amphiphilic polymer. In the meantime, it is preferable to use water as the solvent when hexyl dicarbamate cholesteryl pullulan is used.

The amount of the solvent may be one which can dissolve the tranexamate salt and the amphiphilic polymer. The amount of the solvent may vary depending on the kind of the used amphiphilic polymer, etc. but usually 10 to 2000 times of the amount of the tranexamate salt is preferable by weight ratio, and 20 to 500 times is more preferable, and 50 to 200 times is particularly preferable.

In one embodiment of the present invention, for example, when (2-methacryloyloxyethyl phosphorylcholine/stearyl methacrylate) copolymer is used as an amphiphilic molecule, the amount of the polyhydric alcohol (as a solvent) is preferably in a weight ratio of 10 to 200 times, and more preferably 50 to 200 times of the amount of the tranexamate salt.

In another embodiment of the present invention, for example, when hexyl dicarbamate cholesteryl pullulan is used as an amphiphilic molecule, the amount of water (as a solvent) is preferably in a weight ratio of 500 to 2000 times of the amount of the tranexamate salt.

The amount of the solvent may vary depending on the application of the obtained composition for external use. The amount of the solvent may be appropriately decided depending on the application of the composition for external use.

When the tranexamate salt and the amphiphilic polymer are dissolved in water, a water-soluble organic solvent or a mixture thereof in step a), the solvent may be warmed by heating. In this case, it is preferable that the temperature of the solvent be equal to or less than the boiling point of the solvent, and usually 20 to 120° C. is preferable, and 50 to 100° C. is more preferable, and 70 to 90° C. is particularly preferable.

Step b):

In step b), the mixed solution obtained in step a) is added to an aqueous medium.

According to a preferable aspect of the present invention, the addition of the mixed solution obtained in step a) to an aqueous medium allows the amphiphilic polymer to self-associate to form molecular assembly particles with hydrophobic moieties inward and hydrophilic moieties outward in the aqueous medium. According to a preferable aspect of the present invention, since the tranexamate salt is maintained in these molecular assembly particles, the tranexamate salt can be dispersed in the aqueous medium in a stable state without causing aggregates or crystal precipitation of the tranexamate salt.

The particle diameter of the molecular assembly particles formed by the self-association of the amphiphilic molecules in the present invention is not particularly limited, but it is preferable that the median diameter obtained by measuring the particle size distribution with a laser diffraction particle size analyzer ("SALD-7000" produced by SHIMADZU Corporation) is not more than 1.0 µm, more preferably not more than 0.5 µm, and further preferably not more than 0.2 µm. The smaller the molecular assembly particles are, the more preferable it is. The lower limit of the median diameter is ordinarily in the order of 0.02 µm.

The aqueous medium used in step b) is a medium which contains water in an amount of 50% by weight or more, preferably 70% by weight or more, and more preferably 80% by weight or more of the total weight.

The aqueous medium may contain water-soluble ingredients such as a water-soluble organic solvent, a monosaccharide, an oligosaccharide, an amino acid, a salt, a preservative, a surfactant as needed.

The water-soluble organic solvent can be the same as that used in step a).

As for the monosaccharide, oligosaccharide, amino acid, salt, preservative and surfactant, compounds exemplified later as optional ingredients can be used.

The amount of the aqueous medium is not limited in so far as the tranexamate salt, preferably the molecular assembly particles, and the amphiphilic polymer can be sufficiently dispersed, and ordinarily, the weight ratio (amount of the aqueous medium:amount of mixed solution obtained in step a)) is preferably of 0.8 to 100 times, more preferably of 1.0 to 50 times, and preferably 2.0 to 20 times.

The amount of the aqueous medium is chosen appropriately according to the application of the composition for external use.

When the mixed solution obtained in step a) is added into the aqueous medium, the aqueous medium and/or mixed solution may be warmed by heating. In this case, it is preferable that the temperature of the aqueous medium and/or mixed solution be equal to or less than the boiling point of the aqueous medium or mixed solution, and usually 50 to 95° C. is preferable, and 60 to 85° C. is more preferable, and 65 to 75° C. is particularly preferable.

Step c):

In the method of the present invention, the composition obtained in step b) can be used as such as a composition for external use, or the method may optionally include a step c) comprising the addition of the composition obtained in step b) to another composition for external use.

Said another composition for external use of step c) is not limited in so far as the purpose of the present invention is not hindered. Examples thereof include facial cosmetic materials such as face wash, toilet water, liquid cosmetics, milky liquid, cream and packs, and makeup cosmetic materials such as foundation, lipstick, eye shadow, body cosmetic materials, hair cosmetic materials, oral cavity cosmetic materials, aroma cosmetic materials, washing materials and ointments. In this case, the composition for external use of the present invention may be added in substitution for a well-known whitening agent or in addition to a well-known whitening agent.

The whitening agents may be the compounds exemplified later, which can be incorporated as optional ingredients, and examples thereof include ascorbic acid and the salts or derivatives thereof, niacin such as vitamin C3, AHA, BHA, arbutin, kojic acid, lucinol, ellagic acid, camomila ET, tranexamic acid, cycloamino acid derivatives and linoleic acid.

As described above, a composition for external use in which the tranexamate salt is dispersed stably in an aqueous medium can be obtained.

According to a preferable aspect of the present invention, it is considered that when the composition for external use obtained by the method of the present invention is topically applied to the skin, the molecular assembly particles formed by the dry amphiphilic molecules on the skin form lamella layers, and since the tranexamate salt is kept within these lamella layers, it reaches the skin slowly, and thus the effect of the tranexamate salt continues for an extended period of time. In addition, since the tranexamate salt is kept within the molecular assembly particles, the stability of the composition for external use can be maintained even if it is used together with a well-known whitening ingredient.

The composition for external use of the present invention may contain ingredients which can be incorporated in cosmetics or pharmaceutical compositions and which do not deteriorate the purpose and effect of the present invention.

These optional ingredients may be added in the composition for external use obtained in step b) or c), or they may be added beforehand in the solvent in step a) or alternatively, in the aqueous medium in step b).

Examples of ingredients allowed to be used in cosmetics or pharmaceutical compositions include powder components, a liquid oil, a solid fat, a wax, a hydrocarbon, a higher fatty acid, a higher alcohol (preferably an alcohol having 6 or more carbon atoms, and more preferably an alcohol having 10 or more carbon atoms), a synthetic ester oil, a silicone oil, a surfactant, a co-surfactant, a moisturizing agent, a film forming agent, a thickener, a gelling agent, an inorganic mineral, a metal sequestering agent, a lower alcohol, a polyhydric alcohol, a monosaccharide, an oligosaccharide, an amino acid, a plant extract, an organic amine, a polymer emulsion, an antioxidant, an antioxidant aid, a skin nutrient, a vitamin, a blood flow promoter, an antibacterial agent, an anti-inflammatory agent, a cell (skin) activating agent, a keratolytic agent, a refrigerant, an astringent agent, a skin whitening agent, a UV absorber, a browning inhibitor, an antiseptic agent, a pH adjustor, a buffer and a perfume. The ingredients may be appropriately added if needed to produce a desired formulation form according to a conventional method.

Examples of the powder components include inorganic powders, such as talc, kaolin, mica, sericite, white mica, gold mica, a synthetic mica, red mica, black mica, vermiculite, magnesium carbonate, calcium carbonate, aluminum silicate, barium silicate, calcium silicate, magnesium silicate, strontium silicate, a metal tungstate, silica, zeolite, barium sulfate, magnesium sulfate, calcined calcium sulfate (calcined gypsum), calcium phosphate, fluorine apatite, hydroxyapatite, ceramic powder, metallic soap (e.g. zinc myristate, calcium palmitate, aluminum stearate and magnesium stearate) and boron nitride; organic powders, such as polyamide resin powder (nylon powder), polyethylene powder, polymethyl methacrylate powder, polystyrene powder, styrene/acrylic acid copolymer resin powder, benzoguanamine resin powder, polytetrafluoroethylene powder and cellulose powder; metal powder pigments, such as aluminum powder and copper powder; organic pigments, such as a zirconium-, barium-, and aluminum-lakes; and natural colors, such as chlorophyll and β-carotene. Note that the powder components may be hydrophobized.

Examples of the liquid oil include avocado oil, camellia oil, turtle oil, macadamia nut oil, corn oil, mink oil, olive oil, rapeseed oil, yolk oil, sesame oil, persic oil, wheat germ oil, camellia kissi oil, castor oil, linseed oil, safflower oil, cotton seed oil, perilla oil, soybean oil, peanut oil, tea seed oil, Torreya seed oil, rice bran oil, Chinese tung oil, Japanese tung oil, jojoba oil, germ oil, and triglycerin.

Examples of the solid fat include cacao butter, coconut oil, horse tallow, hardened coconut oil, palm oil, palm kernel oil, Japan tallow kernel oil, hardened oil, Japan tallow, and hardened castor oil.

Examples of the wax include beeswax, candelilla wax, cotton wax, carnauba wax, bayberry wax, Chinese insect wax, montan wax, bran wax, lanolin, kapok wax, acetylated lanolin, liquid lanolin, sugar cane wax, lanolin fatty acid isopropyl ester, hexyl laurate, reduction lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of the hydrocarbon oil include liquid paraffin, ozokerite, squalane, pristane, paraffin, ceresin, squalene, vaseline, microcrystalline wax, and hydrogenated polydecene, isododecane.

Examples of the higher fatty acid include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), and docosahexaenoic acid (DHA).

Examples of the higher alcohol include linear alcohols, such as lauryl alcohol, cetyl alcohol, stearyl alcohol, behenyl alcohol, myristyl alcohol, oleyl alcohol, and cetostearyl alcohol; branched alcohols, such as monostearyl glyceryl ether (batyl alcohol), 2-decyltetradecanol, lanolin alcohol, cholesterol, phytosterol, hexyldodecanol, isostearyl alcohol, and octyldodecanol.

Examples of the synthetic ester oil include tripropylene glycol dineopentanoate, isononyl isononanoate, isotridecyl isononanoate, isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, acetylated lanolin, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprylate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, glyceryl trioctanoate, glyceryl triisopalmitate, trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate, bis-behenyl/isostearyl/phytosteryl dimer dilinoleyl dimer dilinoleate, phytosteryl/behenyl/octyldodecyl/isostearyl lauroyl glutamate, and tri(caprylic acid/capric acid) glyceryl, triethylhexanoin.

Examples of the silicone oil include a chain polysiloxane, such as dimethicone, methyl trimethicone, methylphenylpolysiloxane and diphenylpolysiloxane; a cyclic polysiloxane, such as octamethyl cyclotetrasiloxane, decamethyl cyclopentasiloxane and dodecamethyl cyclohexasiloxane; a silicone resin forming a 3D net structure; a silicone rubber; various modified polysiloxanes, such as amino-modified polysiloxane, polyether-modified polysiloxane, alkyl-modified polysiloxane and fluorine-modified polysiloxane.

Examples of silicone elastomers include non-emulsifying organopolysiloxane elastomers or emulsifying organosiloxane elastomers. Examples of the non-emulsifying organopolysiloxane elastomers include dimethicone/vinyl dimethicone crosspolymers, lauryl dimethicone/vinyl dimethicone crosspolymers, and the like. The dimethicone/vinyl dimethicone crosspolymers include products commercially available from DOW CORNING (Midland, Mich.) under the trade name of, for example, DC 9040 and DC 9045; products commercially available from MOMENTIVE under the trade name of SFE 839 and the Velvasil series products; products commercially available from SHIN ETSU under the trade name of, for example, KSG-15, KSG-16, and KSG-18 ([dimethicone/phenyl vinyl dimethicone crosspolymer]); and Gransil™ series products from GRANT INDUSTRIES.

The lauryl dimethicone/vinyl dimethicone crosspolymers include products commercially available from SHIN ETSU under the trade name of, for example, KSG-31, KSG-32, KSG-41, KSG-42, KSG-43, and KSG-44.

Examples of the emulsifying organosiloxane elastomers include polyalkoxylated silicone elastomers, polyglycerolated silicone elastomers, or the like.

The polyalkoxylated silicone elastomers include products commercially available from DOW CORNING under the trade name of, for example, DC9010 and DC9011; products commercially available from SHIN ETSU under the trade name of, for example, KSG-20, KSG-21, KSG-30, KSG-31, KSG-32, KSG-33, KSG-210, KSG-310, KSG-320, KSG-330, KSG-340, and X-226146.

The polyglycerolated silicone elastomers include products commercially available from SHIN ETSU under the trade name of, for example, KSG-710, KSG-810, KSG-820, KSG-830, KSG-840, KSG-31, KSG-32, KSG-41, KSG-42, KSG-43, and KSG-44. In addition, examples of silicone elastomers into which 2 types of branches, i.e., a silicone chain and an alkyl chain have been introduced include products commercially available from SHIN ETSU under the trade name of, for example, KSG-042Z, KSG-045Z, KSG-320Z, KSG-350Z, KSG-820Z, and KSG-850Z.

Silicone elastomers comprising a polyalkyl ether group as pendant or cross linked may also included as components in the composition for external use of the present invention. Particularly suitable silicone elastomers comprising a polyalkyl ether group include compounds with the International Nomenclature of Cosmetic Ingredients (INCI) name: bis-vinyldimethicone/bis-isobutyl PPG-20 crosspolymer, bis-vinyldimethicone/PPG-20 crosspolymer, dimethicone/bis-isobutyl PPG-20 crosspolymer, dimethicone/PPG-20 crosspolymer, and dimethicone/bis-secbutylPPG-20 crosspolymer. Such cross-linked elastomers are available from Dow Corning under the experimental names of SOEB-1, SOEB-2, SOEB-3 and SOEB-4, and under the proposed commercial name of DC EL-8052 IH Si Organic Elastomer Blend. The elastomer particles are supplied pre-swollen in the respective solvents, isododecane (for SOEB 1-2), isohexadecane (for SOEB-3), and isodecyl neopentanoate (for SOEB-4).

The surfactants may include anionic surfactants, cationic surfactants, amphoteric surfactants, lipophilic nonionic surfactants and hydrophilic nonionic surfactants.

Examples of the anionic surfactant include fatty acid soaps (for example, sodium laurate, sodium palmitate, etc.); higher alkyl sulfate ester salts (for example, sodium lauryl sulfate, lauryl potassium sulfate, etc.); alkylether sulfuric ester salts (for example, POE-lauryl sulfuric acid triethanolamine, POE-sodium lauryl sulfate, etc.); N-acyl sarcosine acids (for example, sodium lauroylsarcosinate, etc.); higher fatty acid amide sulfonate (for example, sodium N-myristoyl-N-methyl taurate, coconut oil fatty acid sodium methyltauride, lauryl sodium methyltauride, etc.); phosphate salts (POE-oleyl ether sodium phosphate, POE-stearyl ether phosphoric acid, etc.); sulfosuccinates (for example, sodium di-2-ethylhexylsulfosuccinate, sodium monolauroyl monoethanol amide polyoxyethylene sulfosuccinate, sodium lauryl polypropylene glycol sulfosuccinate, etc.); alkyl benzene sulfonate (for example, linear sodium dodecylbenzenesulfonate, linear dodecyl benzene sulfonic acid triethanolamine, linear dodecyl benzene sulfonic acid, etc.); higher fatty acid ester sulfate ester salts (for example, sodium hydrogenated coconut oil fatty acid glycerine sulfate, etc.); N-acyl glutamate (for example, monosodium N-lauroyl glutamate, disodium N-stearoyl glutaminic acid, monosodium N-myristoyl-L-glutamate, etc.); sulfated oils (for example, Turkey red oil, etc.); POE-alkylether carboxylic acids; POE-alkylarylether carboxylates; α-olefin sulfonates; higher fatty acid ester sulfonates; secondary alcohol sulfuric ester salts; higher fatty acid alkylol amidosulfuric acid ester salts; lauroyl monoethanol amide sodium succinates; N-palmitoyl aspartic acid ditriethanolamine; sodium casein.

Examples of the cationic surfactant include alkyltrimethylammonium salts (for example, stearyl chloride trimethylammonium, lauryl chloride trimethylammonium, etc.); alkylpyridinium salts (for example, cetylpyridinium chloride, etc.); chloride distearyl dimethylammonium dialkyl dimethyl ammonium salt; poly(N,N'-dimethyl-3,5-methylene piperidium) chloride; alkyl quaternary ammonium salts; alkyl dimethylbenzyl ammonium salts; alkyl isoquinolinium salts; dialkylmorpholium salts; POE-alkylamine; alkylamine salts; polyamine fat acid derivatives; amylalcohol fat acid derivatives; benzalkonium chloride; benzethonium chloride.

Examples of the amphoteric surfactant include imidazoline type ampholytic surfactants (for example, sodium 2-undecyl-N,N,N-(hydroxyethylcarboxymethyl)-2-imidazoline; 2-cocoyl-2-imidazoliniumhydroxide-1-carboxyethyloxy-2 sodium salt, etc.); betaine-based surfactants (for example, 2-heptadecyl-N-carboxymethyl-N-hydroxyethyl imidazolinium betaine, lauryl dimethylamino acetic acid betaine, alkyl betaine, amide betaine, sulfobetaine).

Examples of the lipophilic nonionic surfactant include a sorbitan fatty acid ester, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; a glyceryl polyglyceryl fatty acid, such as glyceryl monocotton seed oil fatty acid, glyceryl monoerucate, glyceryl sesquioleate, glyceryl monostearate, glyceryl α,α'-oleate pyroglutamate, and glyceryl monostearate malate; a propylene glycol fatty acid ester such as monostearate propylene glycol; a hydrogenated castor oil derivative; a glycerin alkyl ether; and steareth-2.

Examples of the hydrophilic nonionic surfactant include a POE-sorbitan fatty acid ester, such as POE-sorbitan monooleate, POE-sorbitan monostearate, POE-sorbitan monooleate and POE-sorbitan tetraoleate; a POE sorbitol fatty acid ester, such as POE-sorbitol monolaurate, POE-sorbitol monooleate, POE-sorbitol pentaoleate and POE-sorbitol monostearate; a POE-glycerin fatty acid ester, such as POE-glycerin monostearate, POE-glycerin monoisostearate and POE-glycerin triisostearate; a POE-fatty acid ester, such as POE-monooleate, POE-distearate, POE-monodioleate and ethylene glycol distearate; a POE-alkyl ether, such as POE-lauryl ether, POE-oleyl ether, POE-stearyl ether, POE-behenyl ether, POE-2-octyldodecyl ether and POE-cholestanol ether; a Pluronic type surfactant (e.g., Pluronic); a POE-POP-alkyl ether, such as POE-POP-cetyl ether, POE-POP-2-decyltetradecyl ether, POE-POP-monobutyl ether, POE-POP-hydrogenated lanolin, POE-POP-glycerin ether and steareth-21.

Examples of the co-surfactants include higher alcohols. Among them, linear alcohols such as lauryl alcohol, cetyl alcohol, stearyl alcohol, behenyl alcohol, myristyl alcohol, oleyl alcohol, cetostearyl alcohol, and the like, are preferable. Cetyl alcohol is particularly preferable.

Examples of the metal sequestering agent include 1-hydroxyethane-1,1-diphosphonic acid; 1-hydroxyethane-1,1-diphosphonic acid tetrasodium salt; disodium edetate; trisodium edetate; tetrasodium edetate; sodium citrate; sodium polyphosphate; sodium metaphosphate; gluconic acid; phosphoric acid; citric acid; ascorbic acid; succinic acid; edetic acid; and trisodium ethylenediamine hydroxyethyl triacetate.

Examples of the lower alcohol include ethanol, propanol, isopropanol, isobutyl alcohol, and t-butyl alcohol.

Examples of the polyhydric alcohol include a dihydric alcohol, such as ethylene glycol, propylene glycol, pentylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol and octylene glycol; a trihydric alcohol, such as glycerin and trimethylolpropane; a tetrahydric alcohol such as pentaerythritol (e.g., 1,2,6-hexanetriol); a pentahydric alcohol such as xylitol; a hexahydric alcohol, such as sorbitol and mannitol; a polyhydric alcohol polymer, such as diethylene glycol, dipropylene glycol, triethylene glycol, polypropylene glycol and tetraethylene glycol; a dihydric alcohol alkyl ether, such as ethylene glycol monomethyl ether and ethylene glycol monoethyl ether; a dihydric alcohol alkyl ether, such as diethylene glycol monomethyl ether, diethylene glycol monoethyl ether and diethylene glycol monobutyl ether; a dihydric alcohol ether ester, such as ethylene glycol monomethyl ether acetate and ethylene glycol monoethyl ether acetate; a glycerol monoalkyl ether, such as chimyl alcohol, selachyl alcohol and batyl alcohol; and a sugar alcohol, such as sorbitol, maltitol, maltotriose, mannitol, sucrose, erythritol, glucose, fructose, starch sugar, maltose, xylitose, and a reduced alcohol of a starch sugar.

Examples of the monosaccharide include a triose, such as D-glyceryl aldehyde and dihydroxyacetone; a tetrose, such as D-erythrose, D-erythrulose, D-threose and erythritol; a pentose, such as L-arabinose, D-xylose, L-lyxose, D-arabinose, D-ribose, D-ribulose, D-xylulose and L-xylulose; a hexose, such as D-glucose, D-talose, D-psicose, D-galactose, D-fructose, L-galactose, L-mannose and D-tagatose; a heptose, such as aldoheptose and heprose; an octose such as octurose; a deoxy sugar, such as 2-deoxy-D-ribose, 6-deoxy-L-galactose and 6-deoxy-L-mannose; an amino sugar, such as D-glucosamine, D-galactosamine, sialic acid, amino uronic acid and muramic acid; a uronic acid, such as D-glucuronic acid, D-mannuronic acid, L-guluronic acid, D-galacturonic acid and L-iduronic acid.

Examples of the oligosaccharide include sucrose, lactose, maltose, trehalose, cellobiose, gentiobiose, umbilicin, raffinose, gentianose, maltotriose, melezitose, planteose, unbelliferose, stachyose, and verbascose.

Examples of the amino acid include a neutral amino acid, such as threonine and cysteine; and a basic amino acid such as hydroxylysine. Further, as an amino acid derivative, for example, sodium acyl sarcosinate (sodium lauroyl sarcosinate), acyl glutamate, sodium acyl β-alanine, glutathione, and pyrrolidone carboxylic acid may be exemplified.

Examples of the organic amine include monoethanolamine, diethanolamine, triethanolamine, morpholine, triisopropanolamine, 2-amino-2-methyl-1,3-propanediol, and 2-amino-2-methyl-1-propanol.

Examples of the polymer emulsion include an acrylic resin emulsion, a poly(ethyl acrylate) emulsion, an acrylic resin solution, a poly(alkyl acrylate) emulsion, a poly(vinyl acetate) emulsion, and a natural rubber latex.

Examples of the vitamin include vitamins A, $B_1$, $B_2$, $B_6$, C and E and derivatives thereof, pantothenic acid and derivatives thereof and biotin.

Examples of the antioxidants include ascorbic acid and its derivatives such as ascorbyl palmitate, ascorbyl tetraisopalmitate, ascorbyl glucoside, magnesium ascorbyl phosphate, sodium ascorbyl phosphate and ascorbyl sorbate; tocopherol and its derivatives, such as tocopheryl acetate, tocopheryl sorbate, and other esters of tocopherol; dibutyl hydroxytoluene (BHT) and butylated hydroxyanisole (BHA); gallic acid ester; phosphoric acid; citric acid; maleic acid; malonic acid; succinic acid; fumaric acid; cephalin; a hexametaphosphate; phytic acid; ethylenediaminetetraacetic acid; and plant extracts, for instance from *Chondrus cripsus, Rhodiola, Thermus thermophilus*, mate leaves, oak wood, kayu rapet bark, sakura leaves and ylang ylang leaves.

Examples of the moisturizing agent include polyethylene glycol; propylene glycol; dipropylene glycol; glycerin; 1,3-butylene glycol; xylitol; sorbitol; maltitol; mucopolysaccharides such as chondroitin sulfuric acid; hyaluronic acid; sodium hyaluronate, sodium acetyl hyaluronate, mucoitinsulfuric acid; caronic acid; atelo-collagen; cholesteryl-12-hydroxystearate; bile salt; a main component of NMF (natural moisturizing factor), such as a pyrrolidone carboxylic acid salt and a lactic acid salt; amino acids such as urea, cysteine and serine; short-chain soluble collagen; a diglycerin (EO) PO addition product; homo- and copolymers of 2-methacryloyloxyethylphosphorylcholine commercially available from NOF under the name of, for example, Lipidure HM and Lipidure PBM; panthenol; allantoin; PEG/PPG/Polybutylene Glycol-8/5/3 Glycerin commercially available from NOF under the trade name of Wilbride S 753; Trimethylglycine commercially available from Asahi KASEI Chemicals under the trade name of AMINOCOAT; and various plant extracts such as *Castanea sativa* extracts, hydrolyzed hazelnut proteins, *Polianthes tuberosa* polysaccharides, *Argania spinosa* kernel oil, and an extract of pearl containing conchiolin commercially available from Maruzen Pharmaceuticals under the trade name of Pearl Extract™.

Examples of the skin softener include glyceryl polymethacrylate, methyl gluceth-20 and the like.

Examples of the antiaging agent include acyl amino acids (specifically, products commercially available from SEDERMA under the trade name of Maxilip, Matrixyl 3000 or Biopeptide CL, or product commercially available from SEPPIC under the trade name of Sepilift); *Pisum sativum* extracts; hydrolyzed soy proteins; methylsilanol mannuronate; hydrolyzed *cucurbita* pepo seedcake; *Scenedesmus* extract; and the like.

Examples of the anti-pollution agents include *Moringa pterygosperma* seed extracts (specifically, product commercially available from LSN under the trade name of Purisoft); Shea butter extract (specifically, products commercially available from SILAB under the trade name of Detoxyl, a blend of ivy extract, phytic acid and sunflower seed extract (for example, product commercially available from SEDERMA under the trade name of OSMOPUR), and the like.

Examples of the keratolytic agents include α-hydroxy acids (specifically, glycolic, lactic, citric, malic, mandelic or tartaric acid), β-hydroxy acids (specifically, salicylic acid), esters thereof (specifically, $C_{12-13}$ alkyl lactate), and plant extracts containing these hydroxy acids (specifically, *Hibiscus sabdriffa* extracts), and the like.

Examples of the water-soluble polymer include natural polymers such as Arabian gum, carrageenan, karaya gum, tragacanth gum, Quinn seed (marmelo), casein, dextrin, gelatine, sodium pectate, sodium alginate, locust bean gum, guar gum, tala gum, Tamarind gum, glucomannan, xylan, mannan, xanthan gum, agar, pectin, fucoidan, galactomannan, curdlan, gellan gum, fucogel, casein, collagen, starch, sodium hyaluronate, *alcaligenes* polysaccharides, semi-synthetic polymers such as methylcellulose, ethylcellulose, sodium carboxymethylcellulose, hydroxyethylcellulose, hydroxymethylcellulose, hydroxypropylcellulose, methyl hydroxypropylcellulose, hydroxypropyl methylcellulose stearoyl ester, propylene glycol alginate, dialkyl dimethylammonium sulfuric acid cellulose, synthetic polymers such as PVA (polyvinyl alcohol), PVM (polyvinyl methyl ether), PVP (polyvinylpyrrolidone), polyethylene oxide, sodium polyacrylate, carboxyvinyl polymer, acrylates/C10-30 alkyl acrylate crosspolymer and sodium polyacrylate.

Examples of the thickener include clay minerals such as bentonite, hectorite, magunesium aluminum silicate (Veegum), laponite.

Examples of the anti-inflammatory agents include bisabolol, allantoin, tranexamic acid, zinc oxide, sulfur oxide and its derivatives, chondroitin sulfate, and glycyrrhizinic acid and its derivatives (for example, glycyrrhizinates).

The composition for external use of the present invention may contain at least one whitening agent to block the synthesis of structural proteins such as the melanocyte-specific glycoprotein Pmel17 involved in the mechanism of melanogenesis (stage I). Example of such a whitening agent may include the ferulic acid-containing cytovector (water, glycol, lecithin, ferulic acid, hydroxyethylcellulose) commercially available from BASF under the trade name of Cytovector™.

Furthermore, if necessary, the composition for external use of the present invention may contain at least one peptide as described in WO2009/010356.

Furthermore, if necessary, the composition for external use of the present invention may include a whitening agent having an inhibition effect on melanin synthesis and/or an inhibition effect on nanophthalmia-related transcription factor (MITF) expression and/or an anti-tyrosinase activity and/or an inhibition effect on endothelin-1 synthesis. Examples of such a whitening agent may include *Glycyrrhiza glabra* extract commercially available from Maruzen Pharmaceuticals under the trade name of Licorice Extract™.

Furthermore, if necessary, the composition for external use of the present invention may include whitening agents having an antioxidant effect as well, such as vitamin C compounds, which include ascorbate salts, ascorbyl esters of fatty acids or of sorbic acid, and other ascorbic acid derivatives. Specific examples include ascorbyl phosphates (magnesium ascorbyl phosphate, sodium ascorbyl phosphate, and the like), and saccharide esters of ascorbic acid (ascorbyl-2-glucoside, 2-O-α-D-glucopyranosyl L-ascorbate, 6-O-β-D-galactopyranosyl L-ascorbate, and the like). Active agents of this type are commercially available from DKSH under the trade name of Ascorbyl Glucoside™.

Furthermore, if necessary, the composition for external use of the present invention may include other whitening agents. Examples of other whitening agents include pigmentation inhibiting agents such as plant extracts (e.g., *Narcissus tazetta* extracts), cetyl tranexamate (Nikko Chemicals Co., Ltd; trade name: NIKKOL TXC), arbutin, kojic acid, ellagic acid, cysteine, 4-thioresorcin, resorcinol or rucinol or their derivatives, glycyrrhizinic acid, hydroquinone-β-glucoside, and the like.

Furthermore, if necessary, the composition for external use of the present invention may also include organic and/or inorganic sunscreens.

Examples of the organic sunscreens may include dibenzoylmethane derivatives such as butyl methoxydibenzoylmethane (product commercially available from HOFFMANN LA ROCHE under the trade name of Parsol 1789); cinnamic acid derivatives such as octyl methoxycinnamate (product commercially available from HOFFMANN LA ROCHE under the trade name of Parsol MCX), salicylates, para-aminobenzoic acids; β,β'-diphenylacrylate derivatives; benzophenone derivatives; benzylidenecamphor derivatives such as terephtalylidene dicamphor sulphonic acid; phenylbenzimidazole derivatives; triazine derivatives; phenylbenzotriazole derivatives; anthranilic acid derivatives, and the like, all of which may be coated or encapsulated.

Examples of the inorganic sunscreens may include pigments and nanopigments formed from coated or uncoated metal oxides. Examples of the nanopigments include titanium oxide, iron oxide, zinc oxide, zirconium oxide and cerium oxide nanopigments, which are all well known as UV photoprotective agents.

Examples of the antiseptic agent include p-hydroxybenzoate ester (e.g., methylparaben and propylparaben) and phenoxyethanol.

In addition, as additives to be used in the composition for external use of the present invention, those mentioned in International Cosmetic Ingredient Dictionary and Handbook, 13th Edition, 2010, published by the Personal Care Products Council, can be used.

The blending amount of the components is not particularly limited as long as it can be used without departing from the purpose of the present invention. The blending amount is suitably selected depending on a formulation, a product form, etc.

The formulation of the composition for external use of the present invention is arbitrarily selectable. As the formulation, for example, any of a solution type, an emulsion type, a water-oil double layer type, a water-oil-powder triple layer type, a gel type and an oil type can be employed.

The product form of the composition for external use of the present invention is arbitrarily selectable, and the composition is applicable to facial cosmetics, such as a facial cleanser, a face lotion, an essence liquid, a milky lotion, a cream and a pack; makeup cosmetics, such as a foundation, a lipstick and an eye shadow; body makeup products; hair care cosmetics; oral care toiletries; perfumeries; cleansers; and ointments.

According to a preferable aspect of the present invention, the composition for external use of the present invention can exhibit an effect of inhibiting pigmentation of and/or whitening the skin. That is, the present invention provides a cosmetic method which inhibits pigmentation of and/or whitens the skin by the topical application, to the skin, of the composition for external use of the present invention.

According to a preferable aspect of the present invention, inhibition of pigmentation and/or whitening of the skin can be performed by using the composition for external use of the present invention as cosmetic material to make spots or pigmentation thinner.

EXAMPLES

In the following, the present invention will be described by way of Examples and Comparative Examples but the present invention is not limited to these Examples.

Examples 1 to 8

Compositions for external use having the compositions shown in Table 1 were prepared as follows:

The ingredients 1 to 7 were mixed lightly and heated and dissolved at 85±5° C. (mixture 1). In the meantime, the ingredient 9 (purified water) was kept at 70±5° C. and stirred and the mixture 1 was added thereto slowly. Then the resultant mixture was cooled to room temperature (25±5° C.) and the ingredient 8 was added thereto.

TABLE 1

Unit: % by weight

| Ingredient | Example | | | | | | | |
|---|---|---|---|---|---|---|---|---|
| | 1 | 2 | 3 | 4 | 5 | 6 | 7 | 8 |
| 1. Cetyl tranexamate hydrochloride salt*[1] | 0.01 | 0.2 | 0.2 | 0.2 | 0.5 | 1.0 | 3.0 | 0.05 |
| 2. (2-methacryloyloxyethylphosphorylcholine/stearyl methacrylate) copolymer*[2] | 0.1 | 1.0 | 1.0 | 1.0 | 2.0 | 5.0 | 15.0 | — |
| 3. Hexyl dicarbamate cholesteryl pullulan*[3] | — | — | — | — | — | — | — | 0.9 |
| 4. Glycerine | 1.0 | 5.0 | 5.0 | 9.5 | 5.0 | 10.0 | 17.5 | — |
| 5. Butylene glycol | 1.0 | 5.0 | 10.0 | 9.5 | 5.0 | 10.0 | 17.5 | — |
| 6. Purified water | — | — | — | — | — | — | — | 89.1 |
| 7. Methylparaben | 0.2 | 0.2 | — | — | 0.2 | 0.2 | — | 0.2 |
| 8. Phenoxyethanol | — | — | 0.5 | 0.5 | — | 0.5 | 0.5 | 0.1 |
| 9. Purified water | Balance | Balance | Balance | Balance | Balance | Balance | Balance | Balance |
| Total | 100 | 100 | 100 | 100 | 100 | 100 | 100 | 100 |

*[1] A product named as "NIKKOL (registered trademark) TXC" produced by Nikko Chemicals Co., Ltd. was used. Appearance: white to slightly yellowish crystalline powder Melting point: 131 to 135° C., Weight loss on drying: 1.0% or less (105° C., 2 hours)

*[2] A product named as "LIPIDURE (registered trademark)-S" produced by NOF Corporation was used. Appearance: white or pale yellow powder

*[3] A product named as "MEDUSEEDS (registered trademark)-C1" (mixture of hexyl dicarbamate cholesteryl pullulan, butylene glycol, methylparaben, phenoxyethanol and water) produced by NOF Corporation was used. Appearance: transparent liquid Comparative Examples 1 to 5

Compositions for external use having the compositions shown in Table 2 were prepared as follows.

The ingredients 1 to 4 were mixed lightly and heated and dissolved at 85±5° C. (mixture 1). In the meantime, the ingredient 6 (purified water) was kept at 70±5° C. and stirred and the mixture 1 was added thereto slowly. Then the resultant mixture was cooled to room temperature (25±5° C.) and the ingredient 5 was added thereto.

TABLE 2

Unit: % by weight

| Ingredient | Comparative Example | | | | |
|---|---|---|---|---|---|
| | 1 | 2 | 3 | 4 | 5 |
| 1. Cetyl tranexamate hydrochloride salt*[1] | 0.01 | 0.2 | 0.5 | 1.0 | 3.0 |
| 2. Glycerine | 1.0 | 5.0 | 5.0 | 10.0 | 17.5 |
| 3. Butylene glycol | 1.0 | 5.0 | 5.0 | 10.0 | 17.5 |
| 4. Methylparaben | 0.2 | 0.2 | 0.2 | 0.2 | — |
| 5. Phenoxyethanol | — | — | — | 0.5 | 0.5 |
| 6. Purified water | Balance | Balance | Balance | Balance | Balance |
| Total | 100 | 100 | 100 | 100 | 100 |

*[1]A product named as "NIKKOL (registered trademark) TXC" produced by Nikko Chemicals Co., Ltd. was used.
Appearance: white to slightly yellowish crystalline powder
Melting point: 131 to 135° C.,
Weight loss on drying: 1.0% or less (105° C., 2 hours)

Evaluation of Stability on Examples 1 to 8 and Comparative Examples 1 to 5

The compositions for external use according to Examples 1 to 8 and Comparative Examples 1 to 5 were left standing overnight at room temperature (25±5° C.), and presence of aggregates and the crystal precipitation state were observed visually. The results are shown in Tables 3 and 4.

TABLE 3

| | Example 1 | Example 2 | Example 3 | Example 4 | Example 5 | Example 6 | Example 7 | Example 8 |
|---|---|---|---|---|---|---|---|---|
| State after left standing | Semi-transparent | Semi-transparent | Semi-transparent | Semi-transparent | Semi-transparent | Semi-transparent | Semi-transparent | Transparent |

TABLE 4

| | Comparative Example 1 | Comparative Example 2 | Comparative Example 3 | Comparative Example 4 | Comparative Example 5 |
|---|---|---|---|---|---|
| State after left standing | Crystal precipitated | Crystal precipitated | Crystal precipitated | Crystal precipitated | Crystal precipitated |

As shown in Table 3, the cetyl tranexamate hydrochloride salt gave a semitransparent state without forming crystals or aggregates in the compositions for external use according to Examples 1 to 8. It is considered that this is because amphiphilic polymer molecular assembly containing the cetyl tranexamate hydrochloride salt disperses as uniform fine particles. On the other hand, in Comparative Examples 1 to 5, crystals of the cetyl tranexamate hydrochloride salt were present as precipitation.

Evaluation of Particle Size Distribution in Examples 1 to 8

In the compositions for external use according to Examples 1 to 8, the particle size distribution obtained after standing overnight at room temperature (20 to 25° C.) was measured by using a laser diffraction particle size analyzer (SALD-7000, produced by SHIMADZU Corporation).

When samples were put into a flow cell, which had been filled with circulating distilled water in advance, the light intensity distribution varies depending on the amount put into the cell. The samples were put into the flow cell until an appropriate concentration, in which the maximum value of the light intensity distribution may be 35 to 75%, and then the particle size distribution was measured. The results are shown in Table 5 in median diameter.

tranexamate hydrochloride salt dispersed as uniform fine particles in the compositions for external use of Examples 1 to 8.

Examples 9 to 11 and Comparative Examples 6 to 8

Compositions for external use having the compositions shown in Table 6 were prepared as follows.

The ingredients 1 to 4 were mixed lightly and heated and dissolved at 85±5° C. (mixture 1). In the meantime, 10.0% by weight of the ingredient 14 (purified water) was kept at 70±5° C. and stirred and the mixture 1 was added thereto slowly and then the resultant mixture was cooled to room temperature (25±5° C.) (mixture 2). Then the ingredients 5 to 8 and the ingredient 14 (remaining part of purified water) were stirred and mixed at room temperature (25±5° C.) and dissolved and ascorbic acid 2-glucoside aqueous solutions of the ingredients 9 to 13 were further added to these solutions (mixture 3). Furthermore, the mixture 3 and the mixture 2 were stirred and mixed lightly.

TABLE 5

| | Example 1 | Example 2 | Example 3 | Example 4 | Example 5 | Example 6 | Example 7 | Example 8 |
|---|---|---|---|---|---|---|---|---|
| Particle size distribution: Median diameter (nm) | 125 | 105 | 123 | 131 | 164 | 450 | 650 | 22 |

As shown in Table 5, it was confirmed that the molecular assembly of the amphiphilic molecules containing the cetyl

TABLE 6

Unit: % by weight

| Ingredient | Example 9 | Example 10 | Example 11 | Comparative Example 6 | Comparative Example 7 | Comparative Example 8 |
|---|---|---|---|---|---|---|
| 1. cetyl tranexamate hydrochloride salt*[1] | 0.02 | 0.02 | 0.02 | 0.02 | 0.02 | 0.02 |
| 2. (2-methacryloyloxyethyl phosphorylcholine/ stearyl methacrylate) copolymer*[2] | 0.1 | 0.1 | 0.1 | — | — | — |
| 3. Glycerine | 1.0 | 1.0 | 1.0 | 1.0 | 1.0 | 1.0 |
| 4. Butylene glycol | 1.0 | 1.0 | 1.0 | 1.0 | 1.0 | 1.0 |
| 5. Xanthan gum | — | 0.5 | 0.5 | — | 0.5 | 0.5 |
| 6. Glyceryl polymethacrylate aqueous solutions*[3] | 20.0 | — | — | 20.0 | — | 20.0 |
| 7. Methylparaben | 0.2 | — | — | 0.2 | — | 0.2 |
| 8. Phenoxyethanol | — | 0.5 | 0.5 | — | 0.5 | 0.3 |
| Ascorbic acid 2-glucoside aqueous solutions { 9. Ascorbic acid 2-glucoside | — | — | 2.0 | — | — | 2.0 |
| 10. 25% by weight sodium hydroxide | — | — | 0.9 | — | — | 0.9 |
| 11. Citric acid | — | — | 0.033 | — | — | 0.033 |
| 12. Disodium hydrogenphosphate | — | — | 0.59 | — | — | 0.59 |
| 13. Purified water | — | — | 5.00 | — | — | 5.00 |
| 14. Purified water | Balance | Balance | Balance | Balance | Balance | Balance |
| Total | 100 | 100 | 100 | 100 | 100 | 100 |

*[1] A product named as "NIKKOL TXC" produced by Nikko Chemicals Co., Ltd. was used. Appearance: white to slightly yellowish crystalline powder Melting point: 131 to 135° C., Weight loss on drying: 1.0% or less (105° C., 2 hours)

*[2] A product named as "LIPIDURE-S" produced by NOF Corporation was used. Appearance: white or pale yellow powder

*[3] A product named as "Lubrajel (registered trademark) MS" (mixture of glyceryl polymethacrylate, propylene glycol, methylparaben, propylparaben and purified water) produced by ISP Japan Ltd. was used.

Evaluation of Stability on Examples 9 to 11 and Comparative Examples 6 to 8

The external preparations for skin according to Examples 9 to 11 and Comparative Examples 6 to 8 were left standing overnight at room temperature (25±5° C.), and presence of aggregates and the crystal precipitation state were observed visually. The results are shown in Table 7.

TABLE 7

|  | Example 9 | Example 10 | Example 11 | Comparative Example 6 | Comparative Example 7 | Comparative Example 8 |
|---|---|---|---|---|---|---|
| State after left standing | Transparent solution | Transparent solution | Transparent solution | Transparent solution containing white aggregates | Transparent solution containing white aggregates | Transparent solution containing white aggregates |

As shown in Table 7, cetyl tranexamate hydrochloride salts in the compositions for external use according to Examples 9 to 11 were obtained as a transparent solution in a state of a uniform fine particle dispersion without forming crystals or aggregates. On the other hand, according to Comparative Examples 6 to 8, aggregates of cetyl tranexamate hydrochloride salts and the other ingredients were present as floating in the transparent solution.

Examples 12 to 17

Compositions for external use of a milky lotion type having the compositions shown in Table 8 were prepared as follows.

The oil phase ingredients 1 to 9 and the aqueous phase ingredients 10 to 18 were heated, stirred and dissolved at 85±5° C. and the oil phase ingredients were added to the aqueous phase ingredients kept to 85±5° C. while stirring. Subsequently the powder ingredient 19 or 20 was added while stirring and the resultant mixture was then cooled to room temperature (25±5° C.) while stirring. Furthermore, in the middle of stirring cooling, ascorbic acid 2-glucoside aqueous solutions (ingredients 21 to 25), whitening ingredients 26 to 29, and a mixed solution of ingredients 30, 31, compositions for external use of Example 4, Example 7 or Example 8 were added thereto.

TABLE 8

Unit: % by weight

|  | Ingredient | Example 12 | 13 | 14 | 15 | 16 | 17 |
|---|---|---|---|---|---|---|---|
| Oil phase | 1. Cetyl alcohol | 2.5 | 2.5 | 2.5 | 3.0 | 3.0 | 3.0 |
|  | 2. Dimethylpolysiloxane | 2.0 | 2.0 | 2.0 | 4.0 | 4.0 | 4.0 |
|  | 3. Squalane | 4.0 | 4.0 | 4.0 | 2.0 | 2.0 | 2.0 |
|  | 4. Glyceryl tri(2-ethylhexanoate) | 2.0 | 2.0 | 2.0 | 2.0 | 2.0 | 2.0 |
|  | 5. Octyldodecyl myristate | — | — | — | 3.0 | 3.0 | 3.0 |
|  | 6. Polyoxyethylene (2) stearyl ether | — | — | — | 2.0 | 2.0 | 2.0 |
|  | 7. Polyoxyethylene (20) stearyl ether | — | — | — | 1.5 | 1.5 | 1.5 |
|  | 8. Decaglyceryl laurate | 2.0 | 2.0 | 2.0 | — | — | — |
|  | 9. Glyceryl monostearate | 1.0 | 1.0 | 1.0 | 2.0 | 2.0 | 2.0 |
| Aqueous phase | 10. Butylene glycol | 2.0 | 2.0 | 2.0 | 2.0 | 2.0 | 2.0 |
|  | 11. Glycerine | 4.0 | 4.0 | 4.0 | 5.0 | 5.0 | 5.0 |
|  | 12. Dipropylene glycol | 2.0 | 2.0 | 2.0 | — | — | — |
|  | 13. Xanthan gum | 0.1 | 0.1 | 0.1 | 0.2 | 0.2 | 0.2 |
|  | 14. Hydroxymethyl cellulose | 0.2 | 0.2 | 0.2 | 0.1 | 0.1 | 0.1 |
|  | 15. Glyceryl polymethacrylate aqueous solutions*[3] | — | — | — | 20.0 | 20.0 | 20.0 |
|  | 16. Methylparaben | 0.2 | 0.2 | 0.2 | — | — | — |
|  | 17. Phenoxyethanol | 0.5 | 0.5 | 0.5 | 0.7 | 0.7 | 0.7 |
|  | 18. Purified water | Balance | Balance | Balance | Balance | Balance | Balance |
| Powder ingredients | 19. Polymethyl methacrylate resin | 2.0 | 2.0 | 2.0 | — | — | — |
|  | 20. Silicone powder | — | — | — | 1.5 | 1.5 | 1.5 |
| Ascorbic acid 2-glucoside | 21. Ascorbic acid 2-glucoside | 2.0 | 2.0 | 2.0 | 2.0 | 2.0 | 2.0 |
|  | 22. 25% by weight sodium hydroxide | 0.9 | 0.9 | 0.9 | 0.9 | 0.9 | 0.9 |

TABLE 8-continued

| | | Example | | | | | | Unit: % by weight |
|---|---|---|---|---|---|---|---|---|
| | Ingredient | | 12 | 13 | 14 | 15 | 16 | 17 |
| aqueous solutions | 23. Citric acid | | 0.033 | 0.033 | 0.033 | 0.033 | 0.033 | 0.033 |
| | 24. Disodium hydrogenphosphate | | 0.59 | 0.59 | 0.59 | 0.59 | 0.59 | 0.59 |
| | 25. Purified water | | 5.00 | 5.00 | 5.00 | 5.00 | 5.00 | 5.00 |
| Whitening ingredients | 26. Licorice extract | | — | — | 1.0 | — | 1.0 | 1.0 |
| | 27. Bunchflower daffodil extract | | — | — | 1.0 | — | 1.0 | 1.0 |
| | 28. Peptide | | — | — | 1.0 | — | 1.0 | 1.0 |
| | 29. Pearl extract | | — | — | 1.0 | — | 1.0 | 1.0 |
| 30. Ethanol | | | — | — | 2.0 | — | 2.0 | 2.0 |
| 31. Flavor | | | — | — | 0.2 | — | 0.2 | 0.2 |
| Composition for external use of Example 4 | | | 1.0 | 10.0 | 1.0 | — | — | — |
| Composition for external use of Example 7 | | | — | — | — | 1.0 | 10.0 | — |
| Composition for external use of Example 8 | | | — | — | — | — | — | 10.0 |
| Total | | | 100 | 100 | 100 | 100 | 100 | 100 |

Comparative Examples 9, 10

Compositions for external use of a milky lotion type having the compositions shown in Table 9 were prepared as follows.

The oil phase ingredients 1 to 9 and the aqueous phase ingredients 10 to 18 were heated, stirred and dissolved at 85±5° C. and the oil phase ingredients were added to the aqueous phase ingredients kept to 85±5° C. while stirring.

Subsequently the powder ingredient 19 or 20 was added while stirring and the resultant mixture was then cooled to room temperature (25±5° C.) while stirring. Furthermore, in the middle of stirring cooling, ascorbic acid 2-glucoside aqueous solutions (ingredients 21 to 25), whitening ingredients 26 to 29, and a mixed solution of ingredients 30, 31, compositions for external use of Comparative Example 2 or Comparative Example 5 were added thereto.

TABLE 9

| | | | Unit: % by weight |
|---|---|---|---|
| | | | Example |
| | Ingredient | 9 | 10 |
| Oil phase | 1. Cetyl alcohol | 2.5 | 3.0 |
| | 2. Dimethylpolysiloxane | 2.0 | 4.0 |
| | 3. Squalane | 4.0 | 2.0 |
| | 4. Glyceryl tri(2-ethylhexanoate) | 2.0 | 2.0 |
| | 5. Octyldodecyl myristate | — | 3.0 |
| | 6. Polyoxyethylene (2) stearyl ether | — | 2.0 |
| | 7. Polyoxyethylene (20) stearyl ether | — | 1.5 |
| | 8. Decaglyceryl laurate | 2.0 | — |
| | 9. Glyceryl monostearate | 1.0 | 2.0 |
| Aqueous phase | 10. Butylene glycol | 2.0 | 2.0 |
| | 11. Glycerine | 4.0 | 5.0 |
| | 12. Dipropylene glycol | 2.0 | — |
| | 13. Xanthan gum | 0.1 | 0.2 |
| | 14. Hydroxymethyl cellulose | 0.2 | 0.1 |
| | 15. Glyceryl polymethacrylate aqueous solutions*3 | — | 20.0 |
| | 16. Methylparaben | 0.2 | — |
| | 17. Phenoxyethanol | 0.5 | 0.7 |
| | 18. Purified water | Balance | Balance |
| Powder ingredients | 19. Polymethyl methacrylate resin | 2.0 | 2.0 |
| | 20. Silicone powder | — | — |
| Ascorbic acid 2-glucoside aqueous solutions | 21. Ascorbic acid 2-glucoside | 2.0 | 2.0 |
| | 22. 25% by weight sodium hydroxide | 0.9 | 0.9 |
| | 23. Citric acid | 0.033 | 0.033 |
| | 24. Disodium hydrogenphosphate | 0.59 | 0.59 |
| | 25. Purified water | 5.00 | 5.00 |
| Whitening ingredients | 26. Licorice extract | 1.0 | 1.0 |
| | 27. Bunchflower daffodil extract | 1.0 | 1.0 |
| | 28. Peptide | 1.0 | 1.0 |
| | 29. Pearl extract | 1.0 | 1.0 |
| 30. Ethanol | | 2.0 | 2.0 |
| 31. Flavor | | 0.2 | 0.2 |
| Composition for external use of Comparative Example 2 | | 1.0 | — |
| Composition for external use of Comparative Example 5 | | — | 1.0 |
| Total | | 100 | 100 |

Evaluation of Stability on Examples 12 to 17 and Comparative Examples 9, 10

The compositions for external use according to Examples 12 to 17 and Comparative Examples 9, 10 were left standing at a high temperature (40±5° C.) respectively for 3 months, and presence of aggregates and the crystal precipitation state were observed visually. The results are shown in Tables 10 and 11.

TABLE 10

| | Example | | | | | |
|---|---|---|---|---|---|---|
| Left standing condition | 12 | 13 | 14 | 15 | 16 | 17 |
| State after left standing at a high temperature for 3 months | White to pale yellow emulsion without aggregates | White to pale yellow emulsion without aggregates | White to pale yellow emulsion without aggregates | White to pale yellow emulsion without aggregates | White to pale yellow emulsion without aggregates | White to pale yellow emulsion without aggregates |

TABLE 11

|  | Comparative Example | |
| --- | --- | --- |
| Left standing condition | 9 | 10 |
| State after left standing at a high temperature for 3 months | White to pale yellow emulsion with brown aggregates contained therein | White to pale yellow emulsion with brown aggregates contained therein |

As shown in Tables 10 and Table 11, when the compositions for external use were left standing at a high temperature, no presence of aggregates was recognized in the white to pale yellow milky lotion in the case of those according to Examples 12 to 17. However, presence of brown-colored aggregates was recognized in the white to pale yellow milky lotion in the case of those according to Comparative Examples 9 and 10.

INDUSTRIAL APPLICABILITY

The composition for external use of the present invention is favorably applicable to drugs, quasi drugs and cosmetics. The composition for external use of the present invention can be utilized in various formulation and product forms. According to a preferable aspect of the present invention, composition for external use of the present invention can exhibit effects of inhibiting pigmentation of and/or whitening the skin by the topical application thereof to the skin.

The invention claimed is:

1. A method for stably dispersing a physiologically acceptable salt of a tranexamate in an aqueous medium, the method comprising steps of:
   (a) dissolving the physiologically acceptable salt of a tranexamate and an amphiphilic polymer, at a weight ratio of 1:4 to 1:10, in water, a water-soluble organic solvent or a mixture thereof, so as to form a mixed solution; and
   (b) adding the mixed solution obtained in step (a) to an aqueous medium, wherein the tranexamate is stably dispersed in the aqueous medium,
   wherein the physiologically acceptable salt of tranexamate is cetyl tranexamate hydrochloride,
   the amphiphilic polymer is a 2-methacryloyloxyethyl phosphorylcholine/stearyl methacrylate copolymer, and
   the water-soluble organic solvent is selected from the group consisting of lower alcohols having 1 to 5 carbon atoms, polyhydric alcohols, and mixtures thereof.

2. The method according to claim 1, wherein the aqueous medium comprises water in an amount of 60 wt % or more.

3. The method according to claim 1, wherein in step (a), the mixture containing the physiologically acceptable salt of the tranexamate, the amphiphilic polymer and the solvent is heated at a temperature of from 20° C. to 120° C. to obtain the mixed solution.

4. The method according to claim 1, wherein step (b) is performed at a temperature of from 50° C. to 95° C.

5. The method according to claim 1, wherein in step (b), molecular assembly particles comprising the physiologically acceptable salt of the tranexamate are formed.

6. The method according to claim 1, further comprising a step (c) of adding the composition obtained in step (b) to another composition for external use.

7. The method according to claim 5, wherein the molecular assembly particles comprise hydrophobic moieties inward and hydrophilic moieties outward in the aqueous medium, and wherein the cetyl tranexamate hydrochloride is maintained in the molecular assembly particles.

8. The method according to claim 5, wherein the molecular assembly particles have a median diameter of not more than 0.2 μm.

9. The method according to claim 1, wherein the water soluble organic solvent is selected from the group consisting of methanol, ethanol, propanol, isopropanol, ethylene glycol, 1,3-butylene glycol, propylene glycol, dipropylene glycol, isoprene glycol, polyethylene glycol, polyoxyethylene methylglucoside, glycerine, diglycerol, and mixtures thereof.

* * * * *